US010603390B2

(12) United States Patent
Chen et al.

(10) Patent No.: US 10,603,390 B2
(45) Date of Patent: Mar. 31, 2020

(54) REAL-TIME FEEDBACK SYSTEM CONTROL TECHNOLOGY PLATFORM WITH DYNAMICALLY CHANGING STIMULATIONS

(71) Applicant: THE REGENTS OF THE UNIVERSITY OF CALIFORNIA, Oakland, CA (US)

(72) Inventors: Yong Chen, Los Angeles, CA (US); Chih-Ming Ho, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 742 days.

(21) Appl. No.: 14/908,516

(22) PCT Filed: Jul. 29, 2014

(86) PCT No.: PCT/US2014/048703
§ 371 (c)(1),
(2) Date: Jan. 28, 2016

(87) PCT Pub. No.: WO2015/017449
PCT Pub. Date: Feb. 5, 2015

(65) Prior Publication Data
US 2016/0206757 A1 Jul. 21, 2016

Related U.S. Application Data

(60) Provisional application No. 61/859,673, filed on Jul. 29, 2013.

(51) Int. Cl.
| | | |
|---|---|---|
| A61K 49/00 | (2006.01) | |
| G16C 99/00 | (2019.01) | |
| G01N 33/50 | (2006.01) | |
| G16H 50/50 | (2018.01) | |

(52) U.S. Cl.
CPC .......... *A61K 49/0008* (2013.01); *G16C 99/00* (2019.02); *G01N 33/5008* (2013.01); *G16H 50/50* (2018.01)

(58) Field of Classification Search
CPC ............ A61K 49/0008; G01N 33/5008; G06F 19/12; G06F 19/704; G06F 19/707; G16H 50/50; G16C 60/00; G16C 10/00–20/90
See application file for complete search history.

(56) References Cited

U.S. PATENT DOCUMENTS

| | | | |
|---|---|---|---|
| 8,463,552 B1 | 6/2013 | Black et al. | |
| 2002/0169561 A1 | 11/2002 | Benight et al. | |
| 2007/0253903 A1 | 11/2007 | Knab et al. | |
| 2009/0012717 A1 | 1/2009 | Lanzara | |
| 2009/0028968 A1 | 1/2009 | Tam et al. | |
| 2009/0075360 A1 | 3/2009 | Ho et al. | |
| 2010/0125241 A1 | 5/2010 | Prud'Homme et al. | |

FOREIGN PATENT DOCUMENTS

| | | | |
|---|---|---|---|
| JP | 2004-510961 A | 4/2004 | |
| JP | 2006-523457 A | 10/2006 | |
| JP | 2007-510970 A | 4/2007 | |
| JP | 2008-502326 A | 1/2008 | |
| JP | 2012-527627 A | 11/2012 | |
| JP | 2013-122754 A | 6/2013 | |
| WO | WO 01/26609 A2 | 4/2001 | |
| WO | WO-02/23186 A2 | 3/2002 | |
| WO | WO-2005/086061 A2 | 9/2005 | |
| WO | WO-2009148962 A1 * | 12/2009 | ............ G05B 17/02 |
| WO | WO-2013/071099 A1 | 5/2013 | |

OTHER PUBLICATIONS

Vozeh et al. Feedback control methods for drug dosage optimization: Concepts, classification and clinical application. Clinical Pharmacokinetics, vol. 10, pp. 457-476, 1985. (Year: 1985).*
Wong et al. Closed-loop control of cellular functions using combinatory drugs guided by a stochastic search algorithm. Proceedings of the National Academy of Sciences, USA, vol. 105, No. 13, pp. 5105-5110, Apr. 2008. (Year: 2008).*
Goteti et al. Preclinical pharmacokinetic/pharmacodynamics models to predict synergistic effects of co-administered anti-cancer agents. Cancer Chemotherapy and Pharmacology, vol. 66, pp. 245-254, 2010, published online Oct. 2009. (Year: 2009).*
Fletcher et al. Concentration-controlled compared with conventional antiretroviral therapy for HIV infection. AIDS, vol. 16, No. 4, pp. 551-560, Mar. 2002. (Year: 2002).*
Drusano, GL. Role of pharmacokinetics in the outcome of infections. Antimicrobial Agents and Chemotherapy, vol. 32, No. 3, pp. 289-297, Mar. 1988. (Year: 1988).*
Le Trouneau et al. Dose escalation methods in Phase I cancer clinical trials. Journal of the National Cancer Institute. vol. 101, No. 10, pp. 708-720, May 2009. (Year: 2009).*
Lu et al. Exposure-response relationship of AMG 386 in combination with weekly paclitaxel in recurrent ovarian cancer and its implication for dose selection. Cancer Chemotherapy and Pharmacology, vol. 69, pp. 1135-1144, Jan. 2012. (Year: 2012).*
Sen et al. Effect of physical parameters, carbon and nitrogen sources on the production of alkaline protease from a newly isolated Bacillus pseudofirmus SVB1. Annals of Microbiology, vol. 59, No. 3, pp. 531-538, 2009. (Year: 2009).*
Jonker et al. Towards a mechanism-based analysis of pharmacodynamic drug-drug interactions in vivo. Pharmacology & Therapeutics, vol. 106, pp. 1-18, 2005. (Year: 2005).*

(Continued)

*Primary Examiner* — Jennifer Dunston
(74) *Attorney, Agent, or Firm* — Foley & Lardner LLP; Mark J. Danielson

(57) ABSTRACT

A method includes: (1) applying stimulations to a system, wherein applying the stimulations includes modulating, over time, characteristics of the stimulations; (2) measuring a time-varying response of the system to the stimulations; (3) fitting the time-varying response of the system into a model of the system; and (4) using the model of the system, identifying an optimized combination of characteristics of the stimulations to yield a desired response of the system.

4 Claims, 5 Drawing Sheets

(56) References Cited

OTHER PUBLICATIONS

Casas et al. Optimization of the reaction parameters for fast psuedo single-phase transesterification of sunflower oil. Fuel, vol. 89, pp. 650-658, 2010. (Year: 2010).*
Calzolari et al., "Search Algorithms as a Framework for the Optimization of Drug Combinations," PLOS Comp. Biol., (2008), vol. 4, No. 12, pp. 1-14.
Extended European Search Report and Search Opinion for European Application No. 14831626.8 dated Dec. 20, 2016.
Feala et al., "Systems Approaches and Algorithms for Discovery of Combinatorial Therapies," Syst. Biol. Med., (2010), vol. 2, No. 2, pp. 181-193.
Wood et al., "Mechanism-Independent Method for Predicting Response to Multidrug Combinations in Bacteria," Proc. Nat. Acad. Sci. USA, (2012), vol. 109, No. 30, pp. 12254-12259.
International Search Report and Written Opinion for International Application No. PCT/US2014/048703 dated Nov. 6. 2014.
Supplementary Examination Written Opinion for Singaporean Patent Application No. 11201600604Q dated Mar. 20, 2018.
Official Action for Japanese Patent Application No. 2016-531831 dated Jul. 10, 2017.
Notice of Intention to Refuse Patent Application for Singaporean Patent Application No. 11201600604Q, dated Jul. 2, 2018.
Official Action for Japanese Patent Application No. 2016-531831, dated May 16, 2018.
Office Action, issued in Chinese Patent Application No. 201480049528. 6, 18 pages (Dec. 3, 2018).
Office Action, issued in Australian Patent Application No. 2014296386, 4 pages (Nov. 6, 2019).

\* cited by examiner

REAL-TIME FEEDBACK SYSTEM CONTROL TECHNOLOGY PLATFORM WITH DYNAMICALLY CHANGING STIMULATIONS

CROSS-REFERENCE TO RELATED APPLICATION

This application is a National Stage Entry of PCT/US2014/048703, filed Jul. 29, 2014, which claims the benefit of U.S. Provisional Application Ser. No. 61/859,673 filed on Jul. 29, 2013, the disclosure of which is incorporated herein by reference in its entirety.

TECHNICAL FIELD

This disclosure generally relates to combinatorial optimization with dynamically changing stimulations.

BACKGROUND

Current drug discovery efforts have primarily focused on identifying agents that tackle specific preselected cellular targets. However, in many cases, a single drug does not correct all of the aberrantly functioning pathways in a disease to produce an effective treatment. Drugs directed at an individual target often have limited efficacy and poor safety profiles due to various factors, including compensatory changes in cellular networks upon drug stimulation, redundancy, crosstalk, and off-target activities. The use of drug combinations that act on multiple targets has been shown to be a more effective treatment strategy.

While a drug combination can be effective, developing optimized drug combinations for clinical trials can be extremely challenging. For example, even a small number of different drugs (six drugs) each tested at a few concentrations (seven dosages) results in $7^6=117,649$ combinations. Screening all 117,649 combinations through in vitro tests for the most desirable combination is an enormous task in terms of labor and time. Also, a drug combination being effective in vitro does not always indicate that the same drug combination would be effective in vivo. Traditionally, when a drug combination is successfully validated in vitro, the combination is applied in vivo, either by keeping the same dosage ratios or by adjusting the drug administration to achieve the same drug blood levels as attained in vitro. This approach can suffer from absorption, distribution, metabolism, and excretion (ADME) issues. ADME describes the disposition of a pharmaceutical compound within an organism, and the four characteristics of ADME can influence the drug levels, kinetics, and, therefore, efficacy of a drug combination. The discontinuity from cell line to animal and from animal to human as a result of ADME poses a major barrier to efficiently identifying optimized drug combinations for clinical trials.

It is against this background that a need arose to develop the combinatorial optimization technique described herein.

SUMMARY

In some embodiments, a method of optimization includes: (1) applying stimulations to a system, wherein applying the stimulations includes modulating, over time, characteristics of the stimulations; (2) measuring a time-varying response of the system to the stimulations; (3) fitting the time-varying response of the system into a model of the system; and (4) using the model of the system, identifying an optimized combination of characteristics of the stimulations to yield a desired response of the system.

In other embodiments, a method of optimization includes: (1) applying a combination of N drugs to a biological system, with N being 2 or more; (2) performing measurements of a time course variation of dosages of the N drugs in the biological system; (3) performing measurements of a time course variation of a therapeutic outcome of the biological system in response to the N drugs; (4) fitting results of the measurements of the dosages and the therapeutic outcome into a model of the therapeutic outcome; and (5) using the model of the therapeutic outcome, identifying an optimized combination of characteristics of the N drugs.

In further embodiments, a method of optimization includes: (1) applying at least one drug to a biological system; (2) performing measurements of a time course variation of a dosage of the drug in the biological system; (3) performing measurements of a time course variation of a therapeutic outcome of the biological system in response to the drug; (4) fitting results of the measurements of the dosage and the therapeutic outcome into a model of the therapeutic outcome; and (5) using the model of the therapeutic outcome, identifying an optimized dosage of the drug, such as an optimized dosage of the drug versus time.

Various models are encompassed by this disclosure, including quadratic models as well as other models, such as ternary and higher order models, among others.

Other aspects and embodiments of this disclosure are also contemplated. The foregoing summary and the following detailed description are not meant to restrict this disclosure to any particular embodiment but are merely meant to describe some embodiments of this disclosure.

BRIEF DESCRIPTION OF THE DRAWINGS

For a better understanding of the nature and objects of some embodiments of this disclosure, reference should be made to the following detailed description taken in conjunction with the accompanying drawings.

DETAILED DESCRIPTION

Overview

Figure 1:
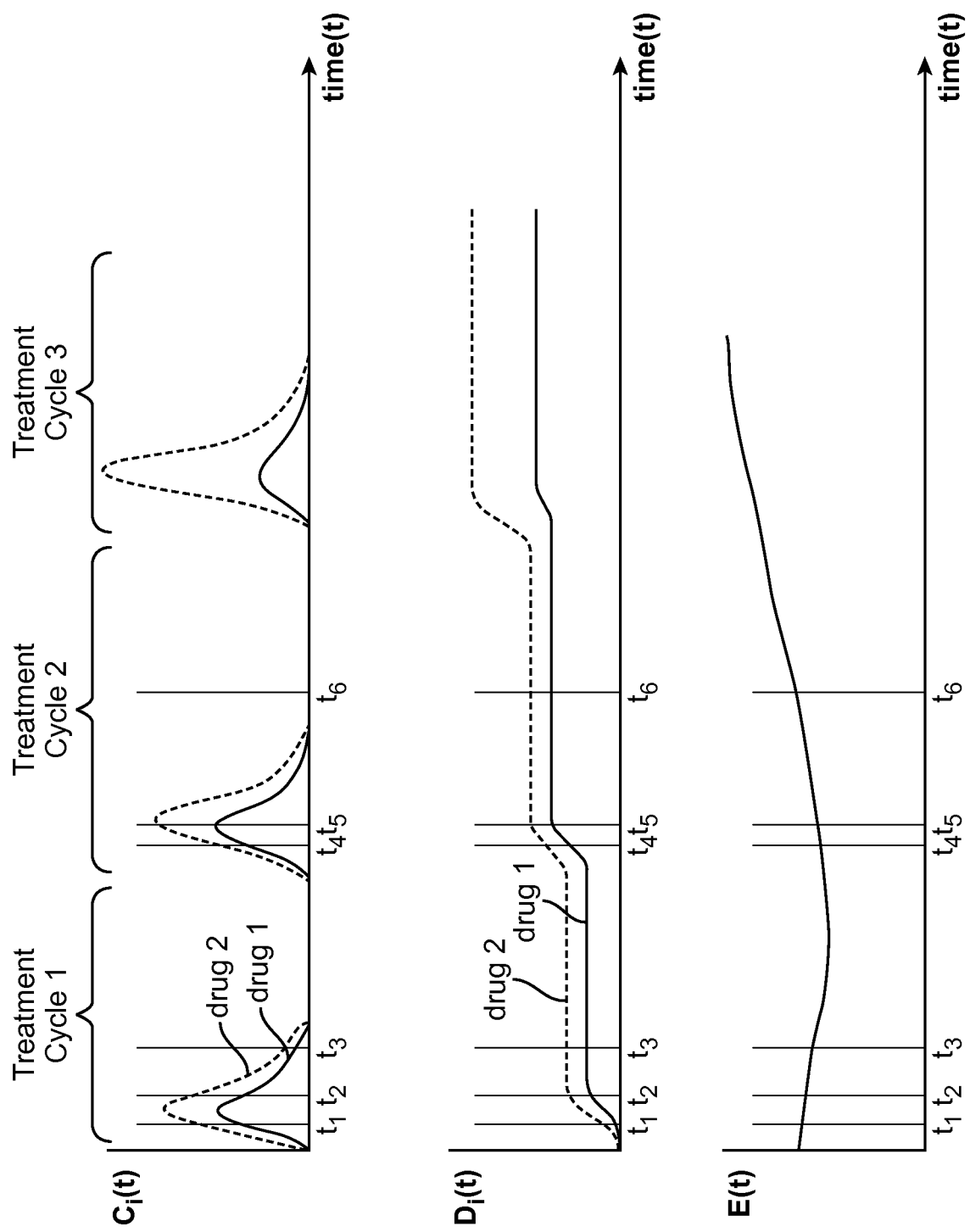
FIG. 1 shows an example of time profiles of drug dosages $C_i(t)$ (upper panel), cumulative drug dosages $D_i(t)$ (middle panel), and a therapeutic outcome E(t) (lower panel) for the case of a combination of 2 drugs (drug 1 and drug 2) applied to a test subject over the course of multiple treatment cycles, according to an embodiment of this disclosure.

Embodiments of this disclosure are directed to identifying optimized combinations of inputs for a complex system. The goal of optimization of some embodiments of this disclosure can be any one or any combination of reducing labor, reducing cost, reducing risk, increasing reliability, increasing efficacies, reducing side effects, reducing toxicities, and alleviating drug resistance, among others. In some embodiments, a specific example of treating diseases of a biological system with optimized drug combinations (or combinatorial drugs) and respective dosages is used to illustrate certain aspects of this disclosure. Identification of optimized drug combinations also can include identification of respective instances of drug application according to certain aspects of this disclosure. A biological system can include, for example, an individual cell, a collection of cells such as a cell culture or a cell line, an organ, a tissue, or a multi-cellular organism such as an animal (e.g., a pet or a livestock), an individual human patient, or a group of human patients. A biological system can also include, for example, a multi-tissue system such as the nervous system, immune system, or cardio-vascular system.

More generally, embodiments of this disclosure can optimize wide varieties of other complex systems by applying pharmaceutical, chemical, nutritional, physical, or other types of stimulations. Applications of embodiments of this disclosure include, for example, optimization of drug combinations, vaccine or vaccine combinations, chemical synthesis, combinatorial chemistry, drug screening, treatment therapy, cosmetics, fragrances, and tissue engineering, as well as other scenarios where a group of optimized system inputs is of interest. For example, other embodiments can be used for 1) optimizing design of a molecule (e.g., drug molecule or protein and aptamer folding), 2) optimizing the docking of a molecule to another molecule for biomarker sensing, 3) optimizing the manufacturing of materials (e.g., from chemical vapor deposition (CVD) or other chemical system), 4) optimizing alloy properties (e.g., high temperature super conductors), 5) optimizing a diet or a nutritional regimen to attain desired health benefits, 6) optimizing ingredients and respective amounts in the design of cosmetics and fragrances, 7) optimizing an engineering or a computer system (e.g., an energy harvesting system, a computer network, or the Internet), 8) optimizing an energy harvesting system, and 9) optimizing a vehicular hybrid energy system (e.g., optimizing fuel, battery efficiency, or both), and 10) optimizing a financial market.

System inputs can be therapeutic stimuli to treat diseases or otherwise promote improved health, such as pharmaceutical (e.g., single drug or combinatorial drugs, including existing and later developed drugs, which are applied towards existing therapeutics, repurposing, and later developed drug optimization), biological (e.g., protein therapeutics, DNA or RNA therapeutics, or immunotherapeutic agents, such as cytokines, chemokines, and immune effector cells such as lymphocytes, macrophages, dendritic cells, natural killer cells, and cytotoxic T lymphocytes), chemical (e.g., chemical compounds, ionic agents, and naturally-derived compounds, such as traditional eastern medicine compounds), physical (e.g., light, heat, electrical stimuli, such as electrical current or pulse, and mechanical stimuli, such as pressure, shear force, or thermal energy, such as through use of nanotubes, nanoparticles, or other nanostructures), among others. Imaging agents can be considered drugs in some embodiments, and these agents can be optimized as well. Examples of imaging agents include magnetic resonance imaging ("MRI") contrast agents (e.g., gadolinium-based, magnesium sulfate-based, and iron oxide-based, among others), computed tomography ("CT") agents, computed axial tomography ("CAT") agents, positron emission tomography ("PET") agents, near-infrared agents, fluorescent agents, nanotechnology-based agents, glucose, and barium-based agents, among others. Optimization of immunotherapy or chemotherapy regimens are encompassed by this disclosure, such as T-cell immunotherapy (e.g., Chimeric Antigen Receptor ("CAR") T-cell therapy and Cytotoxic T Lymphocytes ("CTL"), among others) with optimized combinations to either promote or sustain T-cell activation against cancer. Furthermore, along with immunotherapy or chemotherapy regimens, rapid optimization of drug therapy in concert with such regimens can be attained as well. For example, T-cell immunotherapy with optimized drug combinations can be applied to optimize therapeutic efficacy and safety. In addition, T-cell immunotherapy with optimized combinations of various compounds can be used to optimize T-cell activation to improve treatment efficacy and safety.

Diseases can include, for example, cancer, cardiovascular diseases, pulmonary diseases, atherosclerosis, diabetes, metabolic disorders, genetic diseases, viral diseases (e.g., human immunodeficiency virus, hepatitis B virus, hepatitis C virus, and herpes simplex virus-1 infections), bacterial diseases, and fungal diseases, among others. More generally, the optimization technique of embodiments of this disclosure is applicable towards virtually all classes of diseases, since the diseases mediate phenotypic change which is an output that the optimization technique uses to realize optimal therapeutic outcomes. Optimization can include complete optimization in some embodiments, but also can include substantially complete or partial optimization in other embodiments.

Embodiments of this disclosure provide a number of benefits. For example, current drug discovery efforts rely greatly on high throughput screening ("HTS"), which applies combinatorial screening of millions of chemical, genetic, or pharmacological tests. Such technique has high cost, is labor-intensive, and generates a high amount of waste and low information density data. Besides the intensive labor and cost involved in current in vitro drug screening, another issue with current drug screening lies in the transfer of knowledge between in vitro and in vivo studies. A problem of in vitro experimental studies is that in vitro results sometimes are not able to be extrapolated to in vivo systems and can lead to erroneous conclusions. There are also instances where metabolic enzymes in the body perform very differently between in vitro and in vivo, and these differences can tremendously alter drug activity and potentially increase the risk of underestimation of toxicity. Some embodiments of this disclosure can bypass the above-noted disadvantages of current drug screening. Specifically, some embodiments can effectively replace the intensive labor and cost procedures of in vitro drug screening with a minimal or reduced amount of in vivo studies (e.g., animal studies or clinical or human studies), thereby greatly enhancing the reliability and applicability of experimental results.

Animal testing is used as a tool during drug development, such as to test drug efficacy, identify potential side effects, and identify safe dosage in humans. However, results from animal testing can be very different from that tested in a human patient. In addition, animal testing can be very labor and cost-intensive. Some embodiments of this disclosure can minimize or reduce the use of animals for testing drugs and minimize or reduce the reliance on results from animal testing by applying the disclosed experimental-based technique, which is assisted by modeling, to identify optimal combinations during clinical studies with human patients.

Current efforts in identifying optimized drug combinations have largely focused on 2 or 3 drugs with a few dosages on a trial-by-error basis. When the number of drugs and dosages increase, current combinatorial drug development becomes prohibitive. The challenge of combinatorial drug optimization is further exacerbated when consideration is given towards optimizing respective instances of applying drugs in a combination of drugs. One of the benefits of some embodiments of this disclosure is that the disclosed technique provides a systematic approach to identify optimized drug-dosage combinations as well as optimized drug-dosage-instance combinations.

In addition, different from current drug development efforts, which are often focused on individual signaling pathways or molecular interactions, embodiments of this disclosure can focus on systemic, phenotypically-driven responses, which can be considered as system outputs that are measured or derived over time during the course of a clinical study. Therefore, embodiments of this disclosure can account for complex synergistic and antagonistic interactions inside biological systems that can be hardly revealed in traditional drug screening, including, for example, intracellular signaling pathway processes, linear and non-linear interactions, intermolecular interactions, intercellular interactions, and genotypic interactions and processes. Also, by focusing on systemic, phenotypically-driven responses, the disclosed experimental-based technique can be applied to optimize therapeutic outcomes for a broad range of diseases without reliance on information on underlying biological mechanism, target or targets of drugs, pharmacokinetics, genotypic interactions, or signaling pathways.

Also, considerable efforts are directed towards designing drug combinations for clinical treatment of diseases, such as viral infections, cardiovascular diseases, and cancer, among others. While drug combinations can be designed according to traditional approaches, these approaches typically do not take into account a wide spectrum of disease manifestations. By focusing on a part of the spectrum, a fixed drug combination can ignore heterogeneity among different human patients as well as other potential treatments. Consequently, a segment of human patients may not respond well to a fixed drug combination, or a component of the drug combination may be too toxic or costly to be part of an efficacious treatment. Advantageously, embodiments of this disclosure provide for optimization of case-specific drug combinations, thereby providing a foundation for personalized medicine and, more specifically, phenotypic personalized medicine. In some embodiments, the disclosed technique allows the design of different drug combinations based on different disease manifestations. For example, by adjusting or tuning respective dosages (or dosage ratios) of drugs in a drug combination, a drug combination can be designed to satisfy an individual patient manifestation. Through such case-specific drug design, the design of drug combinations can compromise and balance between different drug design criteria, thereby identifying optimal drug combinations on a case-by-case basis, such as a patient-by-patient basis.

In addition, some embodiments of the disclosed technique can be applied by measuring or deriving time course variations of drug dosages and a therapeutic outcome (e.g., tumor size, drug toxicities, or a combination of both), such that a number of test subjects can be minimized or reduced. Since a very small number of test subjects, even down to one, can be involved in some embodiments, the disclosed technique can greatly minimize or reduce the time and cost for clinical testing, and can be used to identify optimal combinations during clinical testing. The disclosed technique also can realize personalized medicine or phenotypic personalized medicine efficiently.

In addition to optimized combination therapy, the disclosed technique can be used to optimize dosage for a single drug therapy. Readouts from a dynamic, single drug administration can be used to provide an optimized dosage for additional testing or treatment using that single drug.

Optimized Combinations of Inputs for a Complex System

Stimulations can be applied to direct a complex system toward a desired state, such as applying drugs to treat a human patient having a disease. The types and characteristics of the stimulations are part of system inputs that can affect the efficiency in bringing the system toward the desired state, where the characteristics of the stimulations can include their amplitudes (e.g., drug dosages or dosage ratios) and temporal features (e.g., either, or both, time instances and frequencies of drug application). However, N types of different drugs with M possible dosages for each drug will result in $M^N$ possible drug-dosage combinations. And, N types of different drugs with M possible dosages for each drug and each applied in K possible time instants will result in $M^{NK}$ possible combinations. To identify an optimized or even near optimized combination by multiple tests on all possible combinations is prohibitive in practice. For example, it is not practical to perform all possible drug-dosage combinations (or all possible drug-dosage-instance combinations) in animal and clinical tests for finding an effective drug combination as the number of drugs, dosages, and time instances increase.

Some embodiments of this disclosure provide a technique that allows a rapid search for optimized combinations of system inputs to guide multi-dimensional (or multi-variate) engineering, medicine, financial, and industrial problems, as well as controlling other complex systems with multiple inputs toward their desired states. An optimization technique can be used to identify at least a subset, or all, optimized combinations or sub-combinations of inputs that produce desired states of a complex system. Taking the case of combinational drugs, for example, a combination of N drugs can be evaluated to rapidly identify optimized dosages of the N drugs, where N is greater than 1, such as 2 or more, 3 or more, 4 or more, 5 or more, 6 or more, 7 or more, 8 or more, 9 or more, or 10 or more. The optimization technique also can be used to optimize a single drug administration, such that N, more generally, can be 1 or greater than 1.

Some embodiments of this disclosure are based on a surprising finding that an outcome of a complex system in response to multiple inputs can be represented by a low order equation, such as a second order (or quadratic) equation, although a first order (or linear) equation as well as a third order (or cubic) equation are also contemplated as possible low order equations. Also, higher order equations are contemplated for other embodiments. Taking the case of combinational drugs, for example, a therapeutic outcome E can be represented as a function of drug dosages as follows:

$$E(t) = E_0(t) + \sum_i \int_0^t a_i(\tau) C_i(t-\tau) d\tau + \quad (1)$$

$$\sum_{i,i'} \int_0^t \int_0^t a_{ii'}(\tau, \tau') C_i(t-\tau) C_{i'}(t-\tau') d\tau d\tau' + O(C_i C_j C_k)$$

where E(t) is the time-varying therapeutic outcome (e.g., drug efficacy and optionally one or more additional optimization criteria) for a test subject (e.g., a human patient) at time t, $E_0(t)$ is a time-varying baseline therapeutic outcome (e.g., without application of drugs) for the test subject at time t, $C_i(t)$ is a time-varying concentration or dosage (e.g., an external dosage as administered to the test subject or an internal dosage within the test subject, such as a drug blood, saliva, or serum level) of an $i^{th}$ drug at time t, $a_i(\tau)$ is a time-varying first order transfer function between the therapeutic outcome and the $i^{th}$ drug, $a_{ii'}(\tau, \tau')$ is a time-varying second order transfer function between the therapeutic outcome and the $i^{th}$ and $i'^{th}$ drugs representing drug-drug interaction, and the summations run through N corresponding to the total number of drugs in a drug combination being evaluated.

If cubic and other higher order terms are omitted, then the therapeutic outcome E(t) can be represented by a quadratic model as a function of the drug dosages $C_i(t)$. As noted above, other models, including ternary and higher order models or the use of a linear regression model, are also contemplated. Also, although a specific example of combinational drugs is used, it should be noted that the above equation (1) more generally can be used to represent a wide variety of other complex systems as a function of multiple system inputs.

In some embodiments, the therapeutic outcome E(t) can be measured or derived as a weighted combination or a weighted sum of optimization criteria as follows:

$$E(t) = \sum_{k=1}^{n} [w_k \times OC_k(t)] \quad (2)$$

where $OC_k(t)$ is a $k^{th}$ optimization criterion for the test subject at time t, $w_k$ is a weighting factor that can be adjusted or tuned to determine a relative weight of $OC_k(t)$ in optimizing the therapeutic outcome E(t), n is a total number of different optimization criteria being evaluated, and n is 1 or greater than 1, such as 2 or more, 3 or more, 4 or more, 5 or more, 6 or more, 7 or more, 8 or more, 9 or more, or 10 or more. In some embodiments, a sum of all weighting factors is 1 (e.g., $w_1+w_2 \ldots +w_n=1$), although a value of this sum can be varied for other embodiments. In addition to the above equation (2), other representations of the therapeutic outcome E(t) are contemplated and encompassed by this disclosure.

Taking the case of combinatorial drugs, for example, $OC_k(t)$ is the $k^{th}$ optimization criterion in the design of the combination of N drugs. Examples of optimization criteria include drug efficacy, drug toxicity, drug safety, drug side effects, drug tolerance, therapeutic window, and drug cost, among others. In the above equation (2), the therapeutic outcome E(t) represents an overall outcome or response to be optimized (e.g., reduced or minimized, or enhanced or maximized), and is a weighted sum of the n different optimization criteria. In some embodiments, at least one of the n different optimization criteria can correspond to a phenotypic response of the test subject that is subjected to the combination of N drugs. For example, at least one optimization criterion can correspond to drug efficacy, and at least another optimization criterion can correspond to drug safety or toxicity. An optimization criterion can directly correspond a phenotypic response of the test subject, or can be calculated or otherwise derived from one or more phenotypic responses, such as by applying proper transformations to adjust a range and scale of the phenotypic responses.

Certain phenotypic responses are desirable, such as drug efficacy or drug safety, while other phenotypic responses are undesirable, such as drug toxicity or drug side effects. In the case of the latter phenotypic responses, their weighting factors serve as penalty factors in the optimization of the combination of N drugs. Various weighting factors in the above equation (2) can be adjusted or tuned to reflect the relative importance of desirable optimization criteria and undesirable optimization criteria, and the adjustment or tuning can be performed on a case-by-case basis to yield different optimized dosages of the N drugs depending on the particular test subject. Also, the adjustment or tuning of the weighting factors can be performed over time so as to incorporate feedback over the course of a treatment.

Examples of measurements or readouts of phenotypic responses include:

(1) Use of hair, fecal matter, sweat, mucus, cheek swabs, earwax, tears, sperm, skin cells or scrapes, and other excretions or biological materials to screen for markers for tumor treatment response, including proteins and protein fragments, cell, blood, and nucleic acids (e.g., small interfering RNA ("siRNA"), microRNA ("miRNA"), long noncoding RNA, DNA, exosomes, and other classes of ribosomal and deoxyribosomal nucleic acids);

(2) Patient body temperature, blood pressure, pupil dilation, body weight, fluid intake or excretion, and palpation;

(3) Blood draws to monitor levels of circulating tumor markers (e.g., cytokines, antibodies, serum proteins, electrolytes, hematocrit levels, and general protein and biological markers) that serve as indicators for tumor treatment response;

(4) Urine analysis to monitor levels of electrolyte, protein, possible presence of blood, or other markers that serve as indicators for tumor treatment response—additional markers include proteins and protein fragments, cell, and nucleic acids (e.g., siRNA, miRNA, long noncoding RNA, DNA, exosomes, and other relevant nucleic acids);

(5) Sputum analysis to assess number of sperms for infertility treatment and for relevant markers associated with tumor treatment response (e.g., proteins and protein fragments, cell, blood, and nucleic acids, such as siRNA, miRNA, long noncoding RNA, DNA, exosomes, and other classes of ribosomal and deoxyribosomal nucleic acids);

(6) Saliva analysis to assess for relevant markers associated with tumor treatment response (e.g., proteins and protein fragments, cell, blood, and nucleic acids, such as siRNA, miRNA, long noncoding RNA, DNA, exosomes, and other classes of ribosomal and deoxyribosomal nucleic acids);

(7) Use of imaging techniques, such as X-ray, PET, CT, CAT, MRI (e.g., conventional MRI, functional MRI, or other types of MRI), fluorescence spectroscopy, near-infrared spectroscopy, Raman spectroscopy, fluorescence correlation spectroscopy, acoustic imaging techniques, microscopy of tissue, biopsy, and other imaging techniques to monitor tumor size or to monitor fluid and blood flow to and from a tumor as an indicator for tumor treatment response;

(8) Image processing techniques to quantify tumor treatment response from imaging techniques (e.g., pixel counting, heat maps, or other techniques)—image processing techniques also can include image analysis for hematoxylin and eosin staining or other cell or tissue stains to quantify tumor response, fluorescent marker quantification to assess tumor response, and quantification of biopsy (e.g., fine needle aspiration) samples and other relevant biological materials to quantify tumor treatment response; and (9) Skin analysis for accessing color, lipid, and blood circulation for cosmetic treatments.

Referring back to equation (1), if the temporal variation of the baseline therapeutic outcome and the first order and second order transfer functions are assumed to be small or negligible, then the therapeutic outcome E(t) can be represented as follows:

$$E(t) = E_0 + \sum_i a_i D_i(t) + \sum_{ii'} a_{ii'} D_i(t) D_{i'}(t) \quad (3)$$

where $E_0$ is a parameter (e.g., a constant) corresponding to the baseline therapeutic outcome, $a_i$ is a parameter (e.g., a constant) corresponding to the first order transfer function between the therapeutic outcome and the $i^{th}$ drug, $a_{ii'}$ is a parameter (e.g., a constant) corresponding to the second order transfer function between the therapeutic outcome and the $i^{th}$ and $i'^{th}$ drugs, and $D_i(t)$ is a cumulative concentration or dosage (e.g., an integration of the drug dosage $C_i(t)$ over time, such as an integration of a drug blood or serum level over time) of the $i^{th}$ drug applied to the test subject up through time t, and the summations run through N. It is also contemplated that a similar equation as equation (3) can be used to represent the therapeutic outcome E(t) as a function of the drug dosages $C_i(t)$ at time t, and the optimization technique can be similarly applied as explained below.

For the case of N=1 (a total of 1 drug), then:

$$E(t) = E_0 + a_1 D_1(t) + a_{11} D_1(t) D_1(t) \quad (4)$$

with a total of three parameters, $E_0$, $a_1$, and $a_{11}$.

For the case of N=2 (a total of 2 drugs), then:

$$E(t) = E_0 + a_1 D_1(t) + a_2 D_2(t) + a_{12} D_1(t) D_2(t) + a_{11} D_1(t) D_1(t) + a_{22} D_2(t) D_2(t) \quad (5)$$

with a total of six parameters, $E_0$, $a_1$, $a_2$, $a_{12}$, $a_{11}$, and $a_{22}$.

More generally for N total drugs, a total number of parameters m is 1+2N+(N(N−1))/2. If one drug dosage (or its time profile) is kept invariant in the study, the number of parameters m can be further reduced to 1+2(N−1)+((N−1)(N−2))/2, for N>1. Table 1 below sets forth a total number of parameters in a quadratic model of the therapeutic outcome as a function of a total number drugs being evaluated.

TABLE 1

| Drugs (N) | Parameters (m) | Parameters (m) (if one drug dosage is kept invariant) |
|---|---|---|
| 1 | 3 | — |
| 2 | 6 | 3 |
| 3 | 10 | 6 |
| 4 | 15 | 10 |
| 5 | 21 | 15 |
| 6 | 28 | 21 |

By leveraging this surprising finding, a small number of measurements or readouts of drug dosages and phenotypic responses can be performed over time to model a therapeutic outcome-dosage response surface, and this input/output model can be used to identify optimized drug-dosage combinations. Also, by measuring or deriving the time course variations of the drug dosages and the phenotypic responses, the number of test subjects can be minimized or reduced, even down to one, thereby realizing personalized medicine or phenotypic personalized medicine in a clinical setting.

Taking the case of the quadratic model of the therapeutic outcome E(t), for example, multiple measurements or readouts of the drug dosages and the therapeutic outcome can be performed over time for the test subject as follows:

$$E(t_1) = E_0 + \sum_i a_i D_i(t_1) + \sum_{ii'} a_{ii'} D_i(t_1) D_{i'}(t_1) \quad (6)$$

$$E(t_2) = E_0 + \sum_i a_i D_i(t_2) + \sum_{ii'} a_{ii'} D_i(t_2) D_{i'}(t_2)$$

$$\ldots$$

$$E(t_p) = E_0 + \sum_i a_i D_i(t_p) + \sum_{ii'} a_{ii'} D_i(t_p) D_{i'}(t_p)$$

where $E(t_j)$ is the therapeutic outcome measured or derived at time $t_j$ from a total of p measurement instances, and $D_i(t_j)$ is the cumulative dosage of the $i^{th}$ drug measured or derived at time $t_j$ from the total of p measurement instances. From the p measurement instances, the m parameters $E_0$, $a_i$, and $a_{ij}$ can be derived, with p≥m, namely with the number of measurement instances being the same as, or greater than, the number of parameters in the quadratic model of some embodiments. In some embodiments, a reduced number of measurement instances can be conducted, such as with p=m. If one drug dosage (or its time profile) is kept invariant in the study, the number of measurement instances p can be further reduced to 1+2(N−1)+((N−1)(N−2))/2, for N>1. Also, in some embodiments, the number of measurement instances p can be even further reduced, by using interpolation to derive one or more therapeutic outcome values from measured therapeutic outcome values, by using interpolation to derive one or more dosage values from measured dosage values, or both. It is also contemplated that similar equations as equation (6) can be used to represent the therapeutic outcome $E(t_j)$ as a function of the drug dosages $C_i(t_j)$ at particular measurement instances, and the optimization technique can be similarly applied.

FIG. 1 shows an example of time profiles of drug dosages $C_i(t)$ (upper panel), cumulative drug dosages $D_i(t)$ (middle panel), and a therapeutic outcome E(t) (lower panel) for the case of a combination of 2 drugs (drug 1 and drug 2) applied to a test subject over the course of multiple treatment cycles, according to an embodiment of this disclosure. Dosage time profiles for drug 1 are represented by solid curves, while dosage time profiles for drug 2 are represented by dashed curves. In this example, the optimization technique is applied to identify optimized dosages of the 2 drugs that are individually tailored for the test subject and are applied to the test subject in subsequent treatment cycles, based on measurements performed on the test subject during one or more initial treatment cycles. Here, instances (or relative instances) of applying the 2 drugs are kept invariant during the course of treatment, although adjustment and optimization of drug application instances are also contemplated as further explained below. Although the example of 2 drugs is explained with reference to FIG. 1, it will be understood that the optimization technique can be applied to a number of drugs that is more or less than 2.

Referring to FIG. 1, initial dosages of drug 1 and drug 2 are applied to the test subject in treatment cycle 1, and the initial dosages of drug 1 and drug 2 are maintained in treatment cycle 2. During treatment cycles 1 and 2, values of the dosages $C_i(t)$ for drug 1 and drug 2 are measured at multiple measurement instances, here 6 values each for drug 1 and drug 2 at $t_1$ through $t_6$, and the values of dosages $C_i(t)$, in turn, are used to derive values of the cumulative drug dosages $D_i(t)$ for drug 1 and drug 2, here 6 values each for drug 1 and drug 2 at $t_1$ through $t_6$. Also during treatment cycles 1 and 2, values of the therapeutic outcome E(t) are measured at multiple measurement instances, here 6 values at $t_1$ through $t_6$. Although this example sets forth 6 measurement instances of the drug dosages and 6 measurement instances of the therapeutic outcome, less than 6 measurement instances can be performed for either, or both, the drug dosages and the therapeutic outcome, with remaining values derived from a reduced set of measured values through interpolation.

Once measurements are performed on the time course variations of stimulations and an outcome of a complex system in response to the time-varying stimulations, experimental results of the measurements are then fitted into a model of the system by using multi-dimensional fitting, such as regression analysis. Based on the fitting performance between the experimental results and the model, additional measurements can be conducted to improve the accuracy of the model. Once the model with a desired accuracy is achieved, optimized combinations of the stimulations and their optimized characteristics can be identified by using a suitable extreme locating technique, such as by locating global or local maxima in a response surface. Taking the case of the quadratic model of the therapeutic outcome E(t), for example, optimized dosages can be identified once the parameters $E_0$, $a_i$, and $a_{ij}$ are derived through multi-dimensional fitting:

$$E_{max}(t) = E_0 + \sum_i a_i \hat{D}_i(t) + \sum_{ii'} a_{ii'} \hat{D}_i(t) \hat{D}_{i'}(t) \quad (7)$$

where $\hat{D}_i(t)$ is an optimized cumulative dosage of the $i^{th}$ drug applied to the test subject up through time t.

Referring back to the example of FIG. 1, the 6 parameters $E_0$, $a_1$, $a_2$, $a_{12}$, $a_{11}$, and $a_{22}$ of the quadratic model of the therapeutic outcome E(t) can be derived from the 6 measured or derived values of the cumulative drug dosages $D_1(t)$ at $t_1$ through $t_6$, the 6 measured or derived values of the cumulative drug dosages $D_2(t)$ at $t_1$ through $t_6$, and the 6 measured or derived values of the therapeutic outcome E(t) at $t_1$ through $t_6$. Using the quadratic model of the therapeutic outcome E(t), optimized dosages of drug 1 and drug 2 can be identified, and the optimized dosages can be applied to the test subject at a next treatment cycle, here treatment cycle 3. In this example, the optimized dosages of drug 1 and drug 2 identified for the test subject has a lower dosage of drug 1 and a higher dosage of drug 2, relative to the initial dosages of drug 1 and drug 2. Also, the quadratic model of the therapeutic outcome and the optimized dosages of drug 1 and drug 2 can be continually updated over the course of treatment using a moving time window approach, such that time-varying phenotypic responses of the test subject can be accommodated, and the drug dosages can be optimized according to the latest or current phenotype of the test subject. According to the moving time window approach, for example, the drug dosages applied to the test subject at a next treatment cycle 4 can be optimized at least in part based on measurements performed on the test subject during the immediately preceding treatment cycle 3, the drug dosages applied to the test subject at a next treatment cycle 5 can be optimized at least in part based on measurements performed on the test subject during the immediately preceding treatment cycle 4, and so on.

Figure 2:
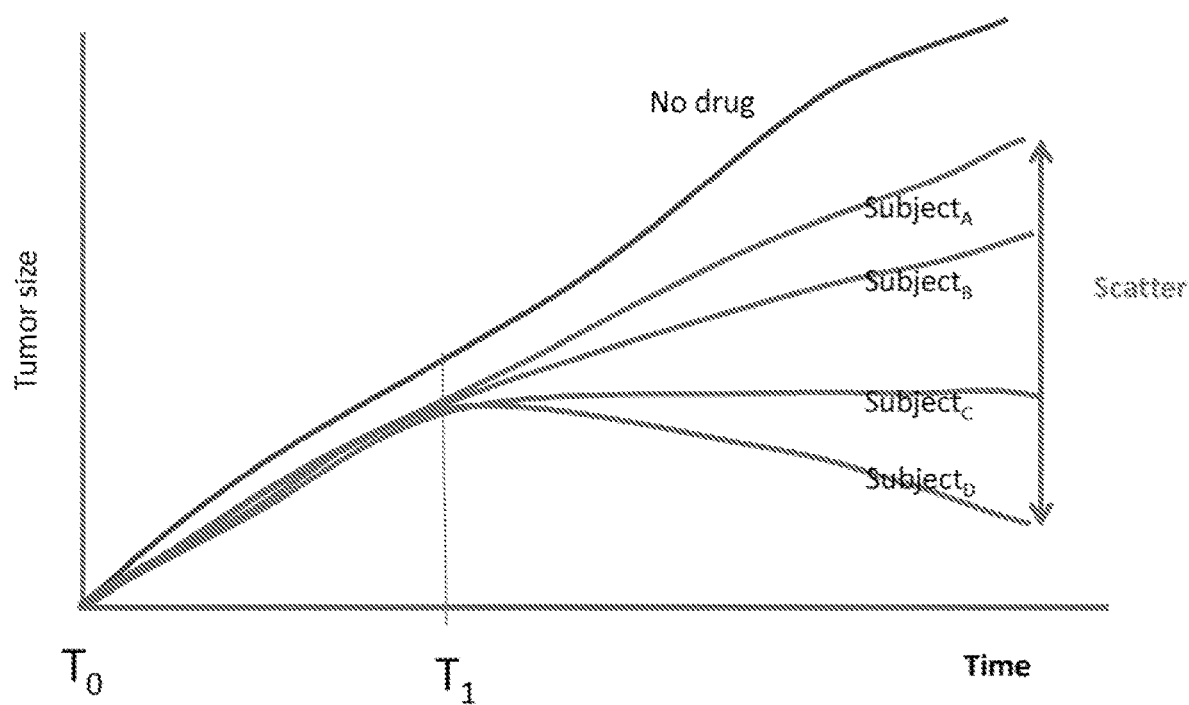
FIG. 2 shows an example of time profiles of therapeutic outcomes for multiple test subjects A through D, for the case of a fixed drug-dosage combination applied to the test subjects starting at time $T_0$, relative to a control time profile in the absence of treatment, according to an embodiment of this disclosure.
Figure 3:
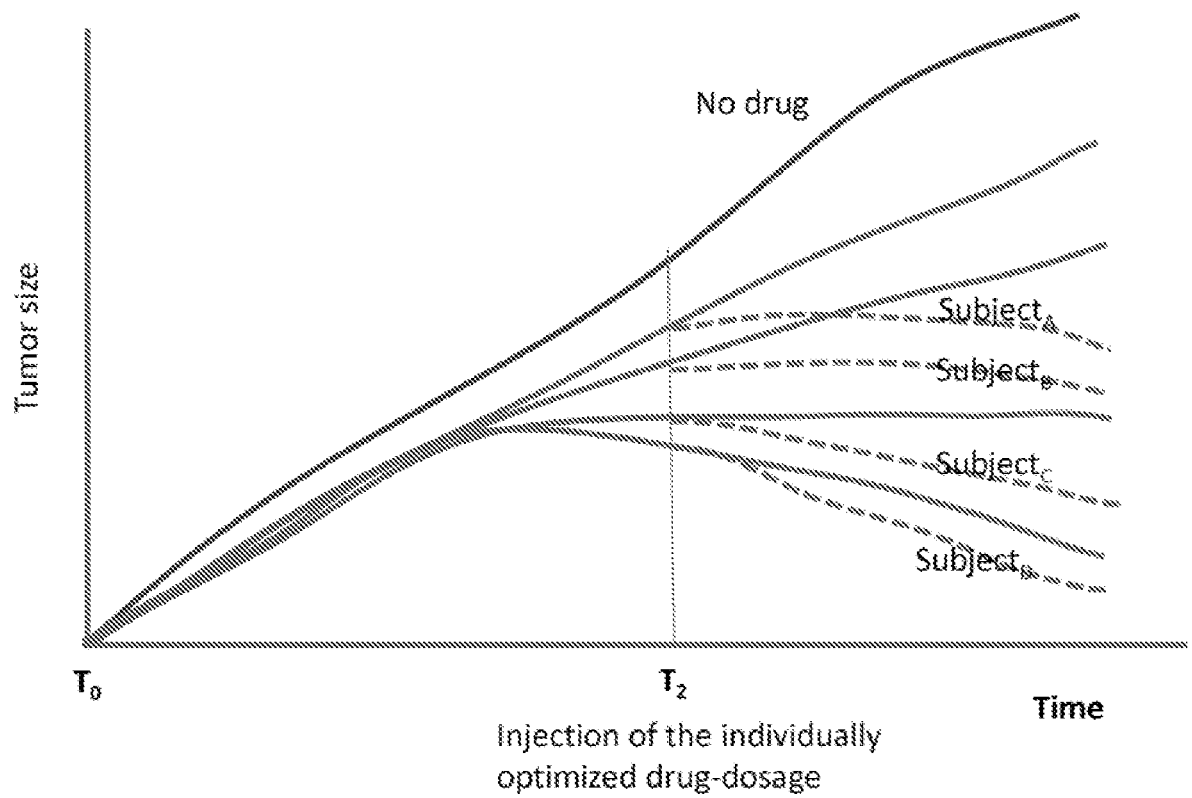
FIG. 3 shows an example of time profiles of therapeutic outcomes for multiple test subjects A through D, for the case of individually optimized drug-dosage combinations respectively applied to the test subjects starting at time $T_2$, relative to a control time profile in the absence of treatment, according to an embodiment of this disclosure.

A further benefit of the disclosed optimization technique is that optimized drug dosages can be individually tailored for a test subject based on phenotypic responses of the test subject to realize phenotypic personalized medicine, and the individually optimized drug dosages for one test subject can differ from those individually optimized for another test subject. FIG. 2 shows an example of time profiles of therapeutic outcomes for multiple test subjects A through D, for the case of a fixed drug-dosage combination applied to the test subjects starting at time $T_0$, relative to a control time profile in the absence of treatment, according to an embodiment of this disclosure. In this example, the therapeutic outcomes are characterized in terms of tumor size. Use of the same, fixed drug-dosage combination across the different test subjects can ignore heterogeneity among the test subjects, and can fail to account for a wide spectrum of disease manifestations. Consequently, the test subjects can respond in varying degrees to the fixed drug-dosage combination, as evidenced by an increasing divergence or scattering of the therapeutic outcomes starting at time $T_1$. In contrast, FIG. 3 shows an example of time profiles of therapeutic outcomes for multiple test subjects A through D, for the case of individually optimized drug-dosage combinations respectively applied to the test subjects starting at time $T_2$, relative to a control time profile in the absence of treatment, according to an embodiment of this disclosure. By adjusting or tuning drug dosages (or drug dosage ratios) according to individual phenotypes, an individually optimized drug-dosage combination can be designed to accommodate an individual disease manifestation. Consequently, there can be a reduced divergence or scattering of the therapeutic outcomes, and a shift toward improved outcomes across the test subjects. Further improvements in the therapeutic outcomes can be attained by continually and individually updating the optimized drug-dosage combinations, according to the moving time window approach.

In some embodiments, an outcome of a complex system in response to stimulations can be sensitive to temporal features (e.g., either, or both, time instances and frequencies) of the stimulations, in conjunction with, or in place of, sensitivity to amplitudes of the stimulations. Advantageously, the optimization technique of this disclosure provides a solution to identifying an optimized single or multiple stimulations with proper amplitudes, time instances, and frequencies, with orders of magnitude of savings in efforts, time, and costs. Specifically, stimulations that are applied dynamically change over time during the course of a study, such as by modulating either, or both, time instances and frequencies at which the stimulations are applied, and measurements are performed on the time course variations of the stimulations. Amplitudes of the stimulations also can be modulated over time during the course of the study. Moreover, the types of the stimulations can be modulated over time during the course of the study. The corresponding dynamically changing outcome of the system is measured, and experimental results of the measurements are then fitted into a model of the system, such as by using multi-dimensional fitting. Based on a correlation between the outcome of the system and the modulation of the amplitudes, time instances, and frequencies (and optionally types of the stimulations), optimized combinations of the amplitudes, time instances, and frequencies (and optionally types of the stimulations) can be identified.

Taking the case of combinatorial drugs, for example, a therapeutic outcome E(t) can be sensitive to time instances and frequencies at which respective drugs in a combination of N drugs are applied, and the disclosed optimization technique can be used to identify optimized time instances and frequencies to apply the drugs. By modulating either, or both, time instances and frequencies at which the drugs are applied and measuring the time course variations of drug dosages and the therapeutic outcome, a correlation between the therapeutic outcome and the time instances and frequencies can be analyzed. Also, transfer functions between the therapeutic outcome and the modulation of the time instances and frequencies during the study can be derived using, for example, a quadratic model. Other models, including ternary and higher order models, are also contemplated. With the transfer functions, optimized time instances and frequencies of applying the drugs can be identified.

Referring to the above equation (1), the first and second order transfer functions can be derived by de-convoluting experimental results of measurements as follows:

$$a_i(\tau) = \left[\int_0^T E(t)\Delta C_i(t-\tau)dt\right] \bigg/ \int_0^T [\Delta C_i(t)]^2 dt \quad (8)$$

$$a_{ii'}(\tau, \tau') = \frac{1}{2}\int_0^T E(t)\Delta C_i(t-\tau)\Delta C_{i'}(t-\tau')dt \bigg/ \int_0^T [\Delta C_i(t)]^2 [\Delta C_{i'}(t)]^2 dt$$

where T is a time period over which the measurements are performed, $$\Delta C_i(t) = C_i(t) - \overline{C}_i$$

where $\overline{C}_i$ is a time-averaged value of $C_i(t)$ over the time period T, and E(t) in the above equation (8) can be replaced by $\Delta E(t)$, given as E(t) minus a time-averaged value of E(t) over the time period T, when the time-averaged value of E(t) is non-zero.

Once the first and second order transfer functions are derived, optimized time instances and frequencies at which the drugs are applied can be derived as follows:

$$\text{Max} E(t) = E_2(t) + \sum_i \int_2^t a_i(\tau)\hat{C}_i(t-\tau)d\tau + \sum_{i,i'} \int_0^t \int_0^t a_{ii'}(\tau, \tau')\hat{C}_i(t-\tau)\hat{C}_{i'}(t-\tau')d\tau d\tau' \quad (9)$$

where $\hat{C}_i(t)$ is an optimized dosage of the $i^{th}$ drug applied to the test subject at time t.

Figure 4:
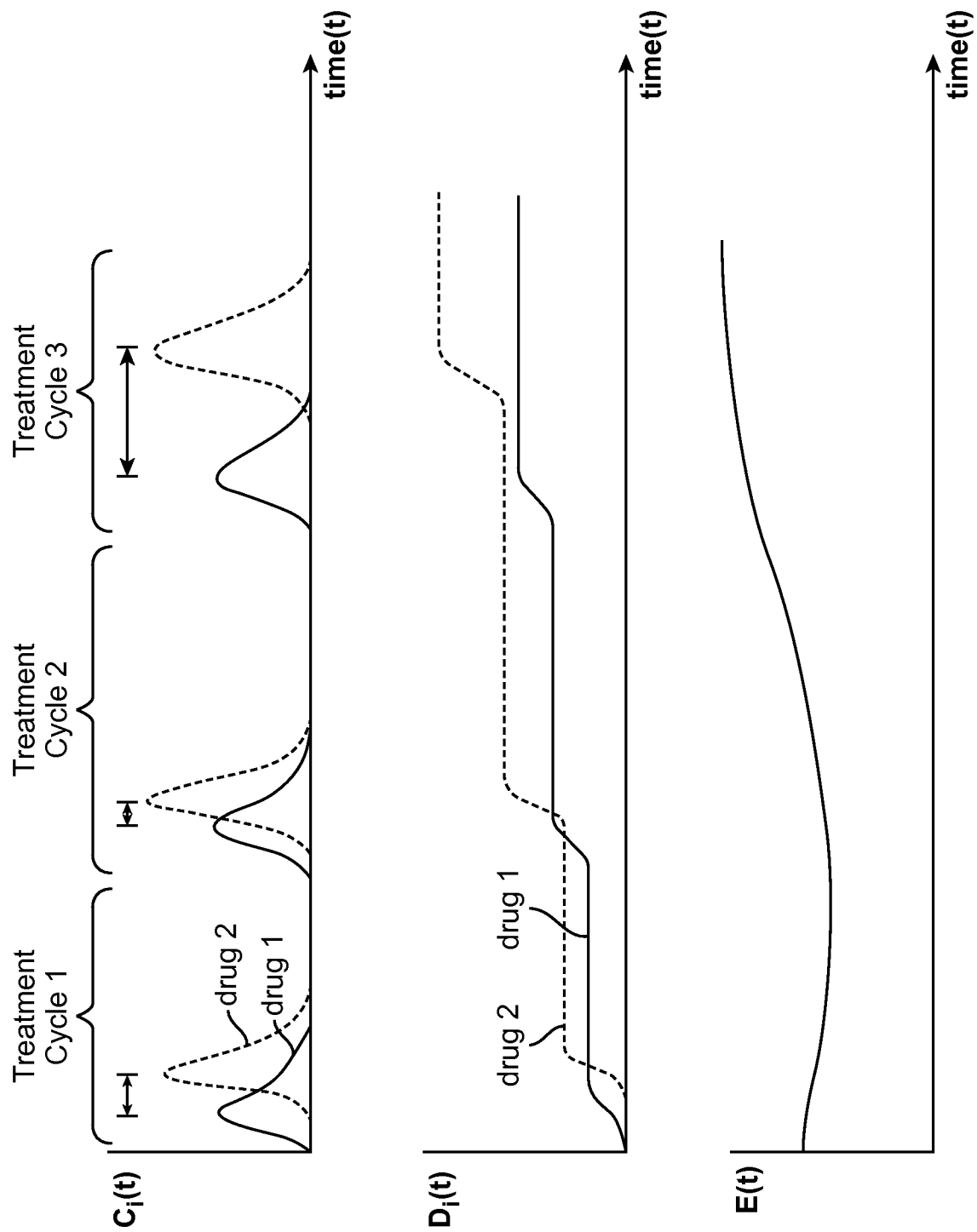
FIG. 4 shows another example of time profiles of drug dosages $C_i(t)$ (upper panel), cumulative drug dosages $D_i(t)$ (middle panel), and a therapeutic outcome E(t) (lower panel) for the case of a combination of 2 drugs (drug 1 and drug 2) applied to a test subject over the course of multiple treatment cycles, according to an embodiment of this disclosure.

FIG. 4 shows another example of time profiles of drug dosages $C_i(t)$ (upper panel), cumulative drug dosages $D_i(t)$ (middle panel), and a therapeutic outcome E(t) (lower panel) for the case of a combination of 2 drugs (drug 1 and drug 2) applied to a test subject over the course of multiple treatment cycles, according to an embodiment of this disclosure. Dosage time profiles for drug 1 are represented by solid curves, while dosage time profiles for drug 2 are represented by dashed curves. In this example, the optimization technique is applied to identify optimized time instances of applying the 2 drugs that are individually tailored for the test subject and are applied to the test subject in subsequent treatment cycles, based on measurements performed on the test subject during one or more initial treatment cycles. Here, a relative time interval between applying the 2 drugs is optimized, characterized, for example, according to a time interval $\Delta t$ between respective peaks of the dosage time profiles $C_i(t)$ of the 2 drugs, although other references points of the dosage time profiles can be used. Also in this example, amplitudes and frequencies of applying the 2 drugs are kept invariant during the course of treatment, although adjustment and optimization of amplitudes and frequencies are also contemplated, such as by modulating a frequency of drug application to greater than once per cycle. Although the example of 2 drugs is explained with reference to FIG. 4, it will be understood that the optimization technique can be applied to a number of drugs that is more or less than 2.

Referring to FIG. 4, drug 1 and drug 2 are applied to the test subject with an initial time interval in treatment cycle 1, and this time interval is modulated in treatment cycle 2. During treatment cycles 1 and 2, values of the dosages $C_i(t)$ for drug 1 and drug 2 are measured at multiple measurement instances, and the values of dosages $C_i(t)$, in turn, can be used to derive values of the cumulative drug dosages $D_i(t)$ for drug 1 and drug 2. Also during treatment cycles 1 and 2, values of the therapeutic outcome E(t) are measured at multiple measurement instances. It is contemplated that a reduced number of measurements can be performed for either, or both, the drug dosages and the therapeutic outcome, with remaining values derived from a reduced set of measured values through interpolation.

Based on the measured or derived values of the drug dosages $C_i(t)$ and the therapeutic outcome E(t), the transfer functions of the quadratic model of the therapeutic outcome E(t) can be derived. Using the quadratic model of the therapeutic outcome E(t), an optimized time interval between applying drug 1 and drug 2 can be identified, and the optimized time interval can be applied to the test subject at a next treatment cycle, here treatment cycle 3. The quadratic model of the therapeutic outcome and the optimized time interval between drug 1 and drug 2 can be continually updated over the course of treatment using a moving time window approach, such that time-varying phenotypic responses of the test subject can be accommodated, and the time interval can be optimized according to the latest or current phenotype of the test subject. Also, the optimized time interval can be individually tailored for the test subject based on phenotypic responses of the test subject, and the individually optimized time interval for the test subject can differ from those individually optimized for another test subject.

Additional aspects and advantages of some embodiments of this disclosure include:

Stimulations: The stimulations can dynamically change over time during the course of a study or treatment (e.g., the stimulations can be applied in a time-varying fashion).

Optimization: An optimized combination of the stimulations (e.g., externally administered drug dosages; drug concentrations in blood, saliva, or serum; time instances; and frequencies) can be identified based on a model during the course of the study or treatment.

Advantages:

(1) Allows single or multi-objective (e.g., efficacy, safety, optimal dosage, and other parameters considered during the course of the study or treatment) optimization of a stimulation during the course of the study or treatment.

(2) Dramatically reduce the time, number, and cost of testing for optimization.

(3) Allows identification of an optimized, time-varying stimulation.

(4) Allows identification of individually optimized stimulations for different test subjects (e.g., personal drug) during the course of the study or treatment.

(5) Does not rely on availability of detailed information for a complex system under control.

(6) Based on a response of the system to designed time-varying stimulations, optimized combinatorial stimulations can be identified in a reduced or minimal number of test cycles, even down to one test cycle.

(7) Stimulations can be applied at different time instances, and optimized time intervals between applying various stimulations can be identified.

(8) Allow direct optimization in animal and clinical tests.

Processing Unit

Figure 5:
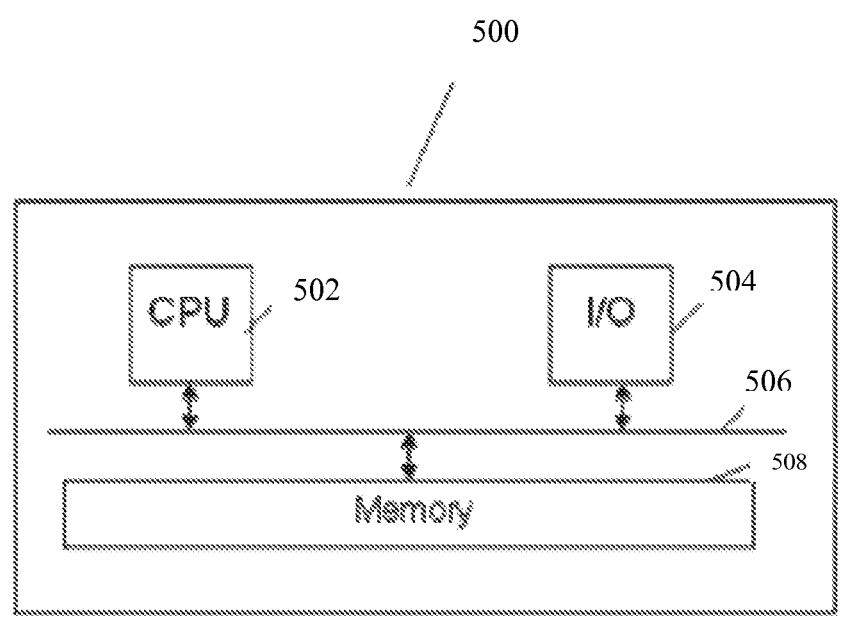
FIG. 5 shows a processing unit implemented in accordance with an embodiment of this disclosure.

FIG. 5 shows a processing unit 500 implemented in accordance with an embodiment of this disclosure. Depending on the specific application, the processing unit 500 can be implemented as, for example, a portable electronics device, a client computer, or a server computer. Referring to FIG. 5, the processing unit 500 includes a central processing unit ("CPU") 502 that is connected to a bus 506. Input/Output ("I/O") devices 504 are also connected to the bus 506, and can include a keyboard, mouse, display, and the like. An executable program, which includes a set of software modules for certain procedures described in the foregoing, is stored in a memory 508, which is also connected to the bus 506. The memory 508 can also store a user interface module to generate visual presentations.

An embodiment of this disclosure relates to a non-transitory computer-readable storage medium having computer code thereon for performing various computer-implemented operations. The term "computer-readable storage medium" is used herein to include any medium that is capable of storing or encoding a sequence of instructions or computer codes for performing the operations described herein. The media and computer code may be those specially designed and constructed for the purposes of this disclosure, or they may be of the kind well known and available to those having skill in the computer software arts. Examples of computer-readable storage media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits ("ASICs"), programmable logic devices ("PLDs"), and ROM and RAM devices. Examples of computer code include machine code, such as produced by a compiler, and files containing higher-level code that are executed by a computer using an interpreter or a compiler. For example, an embodiment of the invention may be implemented using Java, C++, or other object-oriented programming language and development tools. Additional examples of computer code include encrypted code and compressed code. Moreover, an embodiment of this disclosure may be downloaded as a computer program product, which may be transferred from a remote computer (e.g., a server computer) to a requesting computer (e.g., a client computer or a different server computer) via a transmission channel. Another embodiment of this disclosure may be implemented in hardwired circuitry in place of, or in combination with, machine-executable software instructions.

As used herein, the singular terms "a," "an," and "the" include plural referents unless the context clearly dictates otherwise. Thus, for example, reference to an object can include multiple objects unless the context clearly dictates otherwise.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. For example, the terms can refer to less than or equal to ±5%, such as less than or equal to ±4%, less than or equal to ±3%, less than or equal to ±2%, less than or equal to ±1%, less than or equal to ±0.5%, less than or equal to ±0.1%, or less than or equal to ±0.05%.

While the disclosure has been described with reference to the specific embodiments thereof, it should be understood by those skilled in the art that various changes may be made and equivalents may be substituted without departing from the true spirit and scope of the disclosure as defined by the appended claims. In addition, many modifications may be made to adapt a particular situation, material, composition of matter, method, operation or operations, to the objective, spirit and scope of the disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations is not a limitation of the disclosure.

What is claimed is:

1. A method, comprising:
for a combination of N drugs with N being 2 or more, representing a model of a therapeutic outcome as a quadratic function of dosages of the N drugs, wherein the quadratic function includes m parameters, with $m=1+2N+(N(N<1))/2$;
applying the combination of the N drugs to a patient;
performing measurements at p measurement instances of a time course variation of the dosages of the N drugs in the patient, wherein $p \geq m$;
performing measurements at the p measurement instances of a time course variation of the therapeutic outcome of the patient in response to the N drugs;
fitting results of the measurements of the dosages and the therapeutic outcome into the model of the therapeutic outcome;
using the model of the therapeutic outcome to identify optimized dosages of the N drugs; and
treating the patient with the optimized dosages of the N drugs.

2. The method of claim 1, wherein fitting the results of the measurements includes deriving the m parameters.

3. The method of claim 1, wherein N is 3 or more.

4. The method of any one of claims 1, 2, and 3, wherein $p=m$.

* * * * *